United States Patent [19]

Poppendiek et al.

[11] Patent Number: 5,398,694
[45] Date of Patent: Mar. 21, 1995

[54] ANIMAL BIOCALORIMETER AND WASTE MANAGEMENT SYSTEM

[75] Inventors: Heinz F. Poppendiek, La Jolla; William R. Trimailo, Oceanside, both of Calif.

[73] Assignee: Geoscience Ltd., Solana Beach, Calif.

[21] Appl. No.: 987,210

[22] Filed: Feb. 11, 1993

[51] Int. Cl.$^6$ ............................................. A61B 5/00
[52] U.S. Cl. ...................................... 128/718; 374/31; 374/39; 374/41
[58] Field of Search .................. 128/716, 736, 718; 374/31, 40, 39, 33, 34, 41

[56] References Cited

U.S. PATENT DOCUMENTS 4,386,604  6/1983  Hershey ............................... 128/718
5,135,311  8/1992  Alpert .................................. 374/41

Primary Examiner—Lee S. Cohen
Assistant Examiner—Brian M. Green
Attorney, Agent, or Firm—Antonio M. Fernandez

[57] ABSTRACT

A biocalorimeter and waste management system is provided for making metabolic heat release measurements of animals or humans in a calorimeter (enclosure) using ambient air as a low velocity source of ventilating air through the enclosure. A shroud forces ventilating air to pass over the enclosure from an end open to ambient air at the end of the enclosure opposite its ventilating air inlet end and closed around the inlet end of the enclosure in order to obviate the need for regulating ambient air temperature. Psychrometers for measuring dry- and wet-bulb temperature of ventilating air make it possible to account for the sensible and latent heat additions to the ventilating air. A waste removal system momentarily recirculates high velocity air in a closed circuit through the calorimeter wherein a sudden rise in moisture is detected in the ventilating air from the outlet.

7 Claims, 5 Drawing Sheets

ANIMAL BIOCALORIMETER AND WASTE MANAGEMENT SYSTEM

ORIGIN OF INVENTION

This invention is made with Government support under contract NASA-12638 awarded by the National Aeronautics and Space Administration. The Government has certain rights to the invention.

BACKGROUND OF THE INVENTION

This invention relates to a biocalorimeter in general and more particularly to a biocalorimeter that can operate in a space environment for making metabolic heat release measurements of laboratory animals under study by researchers who are investigating the effects of weightlessness. This requires a waste management system for the biocalorimeter.

In the quest for more knowledge about zero-gravity space and about the extent to which man may travel in space, it is contemplated that metabolic heat release measurements will be conducted with caged animals traveling in space. This will require an air ventilation system for maintaining both the life and comfort of the animal with means for removing odors from the air, but in order to make metabolic heat release measurements, the system should also include a waste removal and accumulation system.

One of the problems is preventing wetting of the calorimeter system components. Under zero-gravity conditions, droplets of urine can float in the enclosure and spread over calorimeter components. It is important to provide calorimeters that are free of not only urine but also feces.

When making metabolic heat release measurements with a direct calorimeter system, one of the terms that contributes to the metabolic sum is the evaporative heat transfer from the animal. Normally in a gravity environment, the urine voids are absorbed in some convenient way within the animal cage, such as by providing a shallow layer of mineral oil covered with a grate. Gravity carries the urine through the grate into the mineral oil. But in a zero-gravity environment, droplets of urine will normally float in the air surrounding the animal and finally be deposited on the surfaces of the calorimeter components. Such urine deposition will affect metabolic heat release measurements. This nonprototypic evaporative term distorts the metabolic heat release measurements. Therefore, it is highly desirable to remove urine as well as feces which contain moisture and can become coated with urine. In a more general sense, biological researchers would like to have clean calorimeters system free of urine and feces.

SUMMARY OF THE INVENTION

An object of the invention is therefore to make metabolic heat release measurements of small animals in an enclosure using thermopiles mounted on an inner envelope of the enclosure and electrically connected in series to indicate all of the heat flowing from the interior of the enclosure. This arrangement of an enclosure with a plastic inner envelope and series connected thermopiles is sometimes referred to hereinafter as a biocalorimeter, or more simply a calorimeter, although, as will be noted below, minipsychrometers are also required together with an air flow rate meter to account for animal heat release out of the enclosure via ventilating air circulated through the animal enclosure. The calculations required to determine heat flow rate are made by a computer from the temperature difference measurements made by the thermopile across the gradient layer provided by the plastic envelope, the wet- and dry-air temperature measurements made by the minipsychrometers, and the ventilating air flow rate. A shroud having an opening for allowing ventilating air to flow through the calorimeter shields the biocalorimeter against surrounding radiation heat sources or sinks.

When the biocalorimeter is used in zero-gravity space, such as in a spacecraft, a further object is to remove and store animal waste from the biocalorimeter, including the removal of odors from forced cabin air circulated through the animal enclosure by a pump.

These and other objectives are achieved by psychrometers for measuring dry- and wet-bulb temperature of ventilating air being circulated through the biocalorimeter from the cabin of the spacecraft, a meter for measuring air flow through the biocalorimeter, and means for removing animal waste from the biocalorimeter when a change in moisture is detected by psychrometers that measure wet- and dry-bulb temperature into and out of the animal calorimeter. Waste removal is accomplished by a strong air blower turned on to momentarily force high velocity air in a closed waste removal loop through the biocalorimeter. That forced air sweeps out any animal waste that otherwise floats in the enclosure for the animals undergoing heat release measurements and would otherwise eventually be deposited on surfaces of the calorimeter components.

The internal surface of the biocalorimeter is coated with a hydrophobic material in the form of closely spaced microspheres to provide a network of narrow surface air passages. Any droplets of urine that may be deposited on such coated surfaces will not wet the surface of the microspheres and instead will retain their droplet form due to surface tension. Sweeping air forced through the animal enclosure will then carry the droplets out.

The sweeping air exits the biocalorimeter through a centrifugal flow channel of small cross section so that its velocity is relatively higher. The flow channel redirects the sweeping air through at least 180° to cause the droplets of liquid waste to be forced onto an absorbing surface of the flow channel by a strong centrifugal force. There the droplets are stored for the duration of the mission. Surfaces of this waste removal flow channel as well as the ventilating air channel are coated with odor absorbing material.

The novel features that are considered characteristic of this invention are set forth with particularity in the appended claims. The invention will best be understood from the following description when read in connection with the accompanying drawings.

DESCRIPTION OF PREFERRED EMBODIMENTS

The direct calorimeter principles employed in this invention are first briefly reviewed. The metabolic heat release $q_m$, in animals consists of four heat transfer rate processes, namely convection, evaporation, radiation and body storage.

$$q_m = q_{conv} + q_{evap} + q_{net\ rad} + q_s \tag{1}$$

The convective heat loss term, $q_{conv}$, is defined as the product of the heat transfer conductance, the mean body surface-ambient air temperature difference and the body surface area. The evaporative heat loss term, $q_{evap}$, is equal to the product of the water loss rate and the latent heat of vaporization of water. The net radiant heat loss, $q_{net\ rad}$, is defined as the product of a shape-emissivity function, the body surface area, and the difference in the fourth power absolute body and environmental temperatures. The body heat storage term, $q_s$, may be either positive, negative, or zero, depending on whether the body temperature is rising, falling, or is a constant.

Figure 1:
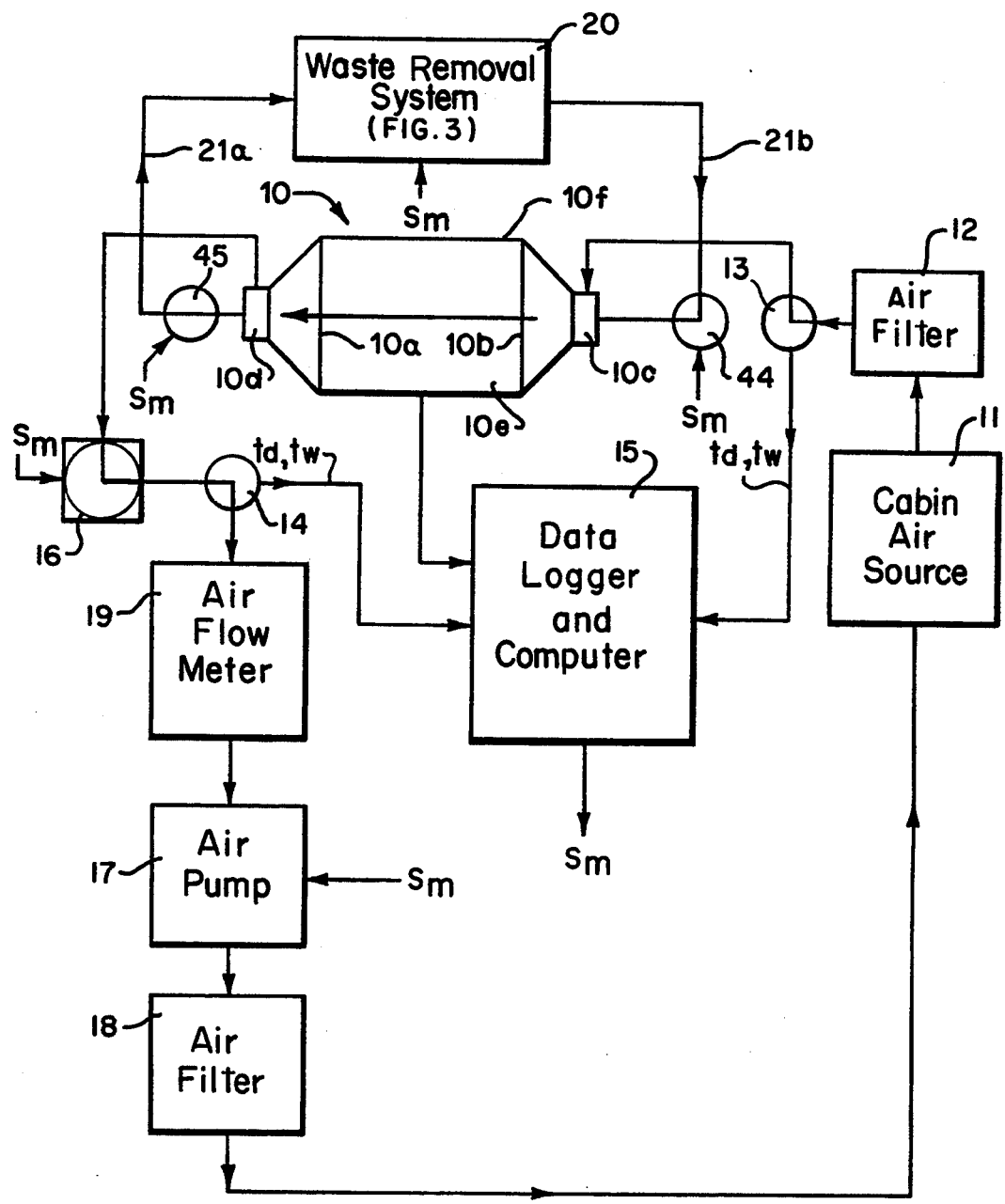
FIG. 1 is a diagram of major elements of a biocalorimeter system including a waste removal air flow system.

FIG. 1 illustrates an arrangement of major elements of a direct animal calorimeter comprising an enclosure 10 having grates 10a and 10b for caging an animal, a continuous source 11 of forced ventilating air into the animal enclosure 10 through an air filter 12, a minipsychrometer 13 at an air inlet 10c of the enclosure 10, and a second minipsychrometer 14 downstream from an air outlet 10d of the enclosure 10. The calorimeter system includes an inner thermopile envelope 10e for measuring heat flow rate. The envelope 10e is preferably made of plastic for electrical isolation of thermopiles electrically connected in series to indicate all the heat flowing from the interior of the calorimeter to an aluminum outer shell 10f serving as a heat sink. This arrangement of thermopiles for measuring temperature difference across the gradient layer of plastic is thus similar to that of a whole human body calorimeter disclosed in U.S. Pat. No. 5,040,541 for a Whole Body Calorimeter by the present inventor, incorporated herein by this reference.

Figure 5A:
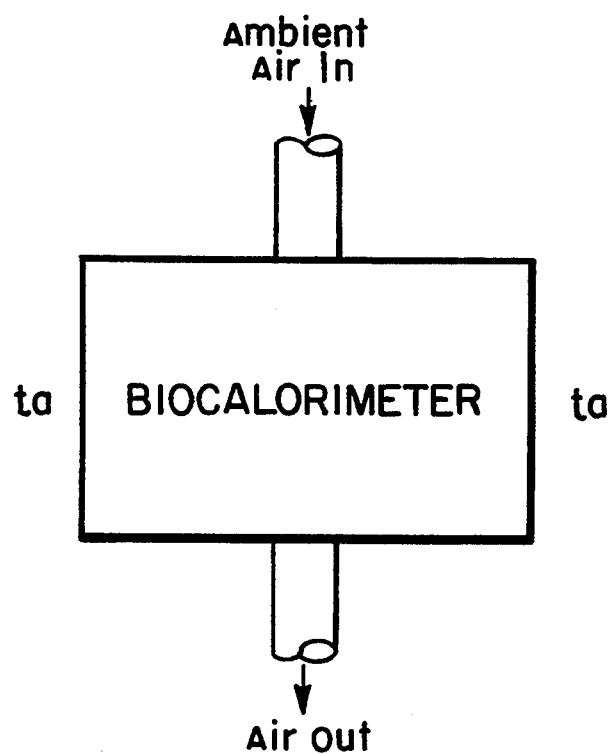
FIG. 5a shows the simplest geometrical deployment of a biocalorimeter envelope relating to situations when there are no strong radiation sources or radiation sinks in the surrounding space.
Figure 5B:
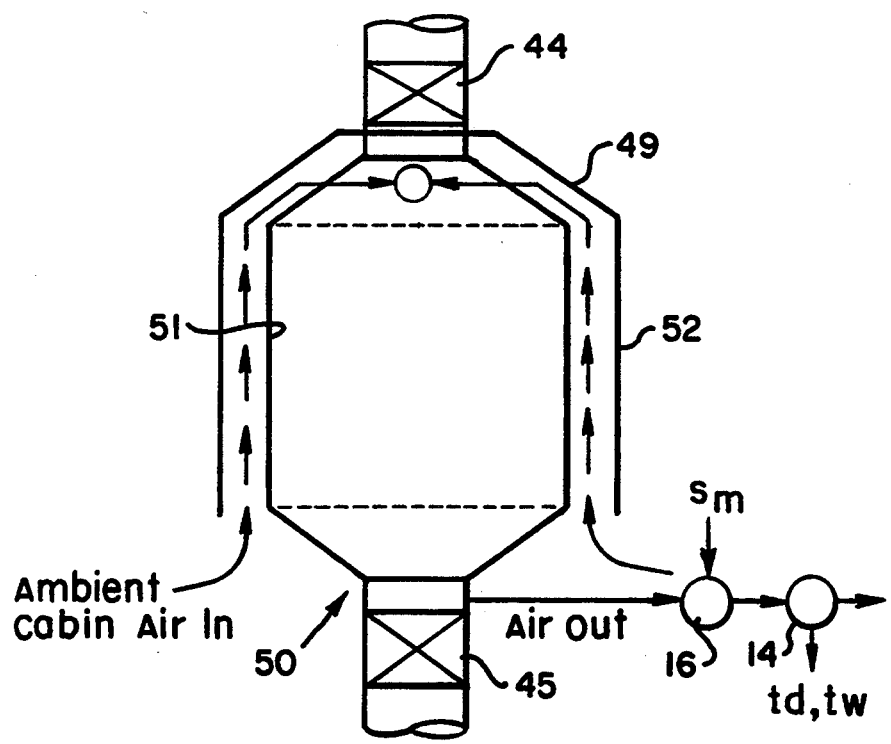
FIG. 5b illustrates an alternative geometrical deployment of a biocalorimeter envelope relating to situations when, as for the present invention, there are strong varying radiation sources or radiation sinks in the surrounding space.

The ventilating air source 11 may be the cabin of a spacecraft which flows into the enclosure 10 through a shroud 52 shown in FIG. 5b around the enclosure 10 to shield the calorimeter from surrounding radiation heat sources or sinks. An isolation valve 16, exhaust air pump (centrifugal or fan) 17 and an exit air filter 18, together with an air flow meter 19 for monitoring flow rate, complete the low velocity air flow channel which provides continuous ventilation for animals in the enclosure 10. That enclosure with thermopiles mounted on an inner envelope 10e to measure heat transfer to the outer heat sink 10f and temperature measuring thermocouples or thermistors in minipsychrometers 13 and 14, comprises the biocalorimeter of the present invention.

One difference in the design of the space calorimeter from earth-based calorimeters relates to the heat removal processes from the calorimeter, and a second difference is in the geometry of the inlet and outlet air flow control through the calorimeter. Instead of cooling the outer surface of the calorimeter by water flow, as shown in the aforesaid U.S. Pat. No. 5,040,541, radiation and forced ventilating air flow through the shroud 52 of FIG. 5b is utilized. The arrangement for the inlet and outlet air flow control, and the inlet and outlet regions of the calorimeter 10 are unique. The inlet and outlet flow regions are pyramidal in shape as shown in FIG. 1 to support flow visualization tests, yielding minimum air flow transit or residence times within the enclosure for prototypical ventilation rates.

A steady state heat rate balance for the system is $$q_m = q_{cal} + q_{sen} + q_{lat} \tag{2}$$

where $q_m$, metabolic heat rate production $q_{cal}$, heat flowing through the plastic thermopile envelope 10e (gradient layer of the calorimeter)

$q_{sen}$, sensible heat flow gained by ventilating air $q_{lat}$, latent heat flow gained by ventilating air (also $q_{evap}$)

The sensible and latent heat flow gains in the ventilating air can be expressed as:

$$q_{sen} + q_{lat} = W_a(i_{out} - i_{in}) \tag{3}$$

where $W_a$, ventilating air flow rate through calorimeter $i_{out}$, air enthalpy out of the calorimeter $i_{in}$, air enthalpy into calorimeter The latent heat gain in the ventilating air can be determined using air temperature data obtained from the minipsychrometer 13 at the inlet and minipsychrometer 14 at the outlet, i.e., by subtracting the sensible heat gain in the ventilating air in from the total heat gain in the ventilating air out, namely $$q_{lat} = W_a(i_{out} - i_{in}) - W_a C_{pa}(t_{dry\ air\ out} - t_{dry\ air\ in}) \tag{4}$$

It is of interest to divide the metabolic heat release into the three steady state heat loss terms, namely, $q_{conv}$, $q_{evap}$, and $q_{net}$ radiation noted in Equation (1). The $q_{lat}$ (or $q_{evap}$) term is determined from Equation (4). The sum of the convective and net radiative losses are equal to the difference in the metabolic term and the latent or evaporative heat loss, namely $$q_{net\ rad} + q_{conv} = q_m - q_{lat} \tag{5}$$

Further, it can be shown that the ratio of the convective to net radiative heat losses can be expressed as $$\frac{q_{conv}}{q_{net\ rad}} = \frac{h_c(t_b - t_i)}{\dfrac{\sigma(T_b^4 - T_w^4)}{\dfrac{1}{\epsilon_b} + \dfrac{A_b}{A_w}\left(\dfrac{1}{\epsilon_w} - 1\right)}} \tag{6}$$

where $h_c$, mean convective conductance for the animal $t_b$, mean surface temperature of the animal $t_i$, mean air temperature inside calorimeter $A_b$, total surface area of the animal $\sigma$, Stefan-Boltzmann constant $\epsilon_b$, surface emissivity of the animal $\epsilon_w$, emissivity of calorimeter inside walls
$A_w$, total surface area of calorimeter inside walls
$T_b$, mean absolute surface temperature of the animal
$T_w$, absolute temperature of the calorimeter inside walls The convective conductances for animals can be defined by convection from short cylinders or from spheres. The emissivities of animal fur is generally very close to unity for the far infrared region involved. The area ratio is determined by the comparative sizes of the animal and calorimeter, sometimes referred to as the animal enclosure. Animal surface, inside air and enclosure wall temperatures are usually measured with thermocouples or thermistors. With such information, the heat flow ratio in Equation (6) can then be calculated with a reasonable accuracy and thus the separation of the sum of the convective and radiative heat releases can be achieved.

The biocalorimeter system may use minipsychrometers (wet- and dry-bulb temperature measurement units) 13 and 14 not only for making metabolic heat release measurements in a known manner but also to detect any step increase in moisture in the ventilating air flow out of the enclosure 10 by analysis of the dry- and wet-temperatures $t_d$ and $t_w$ respectively, which are logged together with ventilating air flow rate from the meter 19 and the heat flow rate from the thermopile envelope 10e by a computer 15. When a step increase in ventilating air is detected by this analysis, the waste removal system 20 is brought into play by a pulse signal $S_m$ but not until after some time has elapsed sufficient for the animal to have completed elimination of urine or feces. Thus, in addition to the ventilating air flow circuit, there is a waste removal system 20 shown in FIG. 3 having sweeping air flow channels 21a and 21b.

Figure 2:
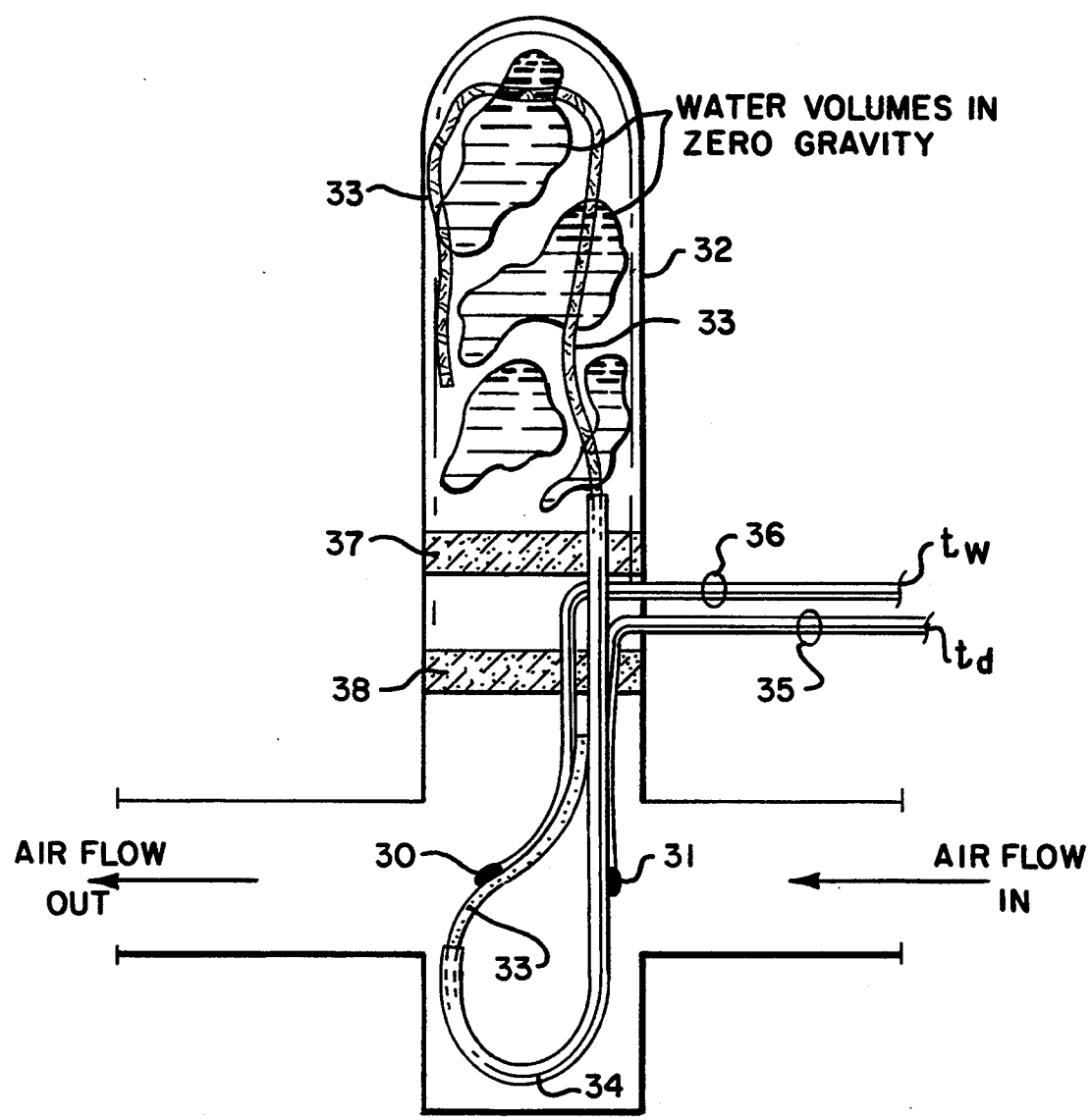
FIG. 2 is a schematic diagram of a minipsychrometer used for elements 13 and 14 in the system of FIG. 1.

These minipsychrometers, shown in FIG. 2, utilize fine gauge thermocouples 30 and 31. Air flows directly over the dry-temperature thermocouple 31 while moisture from a wick 33 extending from a water reservoir 32 wets the other thermocouple 30. The wick passes from the water reservoir 32 through a plastic tube 34 into the air channel. The dry thermocouple 31 is placed upstream from the wick 33. Pairs of leads 35 and 36 provide the respective dry and wet temperature measurement signals $t_d$ and $t_w$ to the computer 15 (FIG. 1) for metabolic heat release measurement and for detection of a step increase in moisture in the ventilating air and metabolic heat release analysis. Moisture barriers 37 and 38 isolate the water reservoir 32 from the air flow channel.

Figure 3:
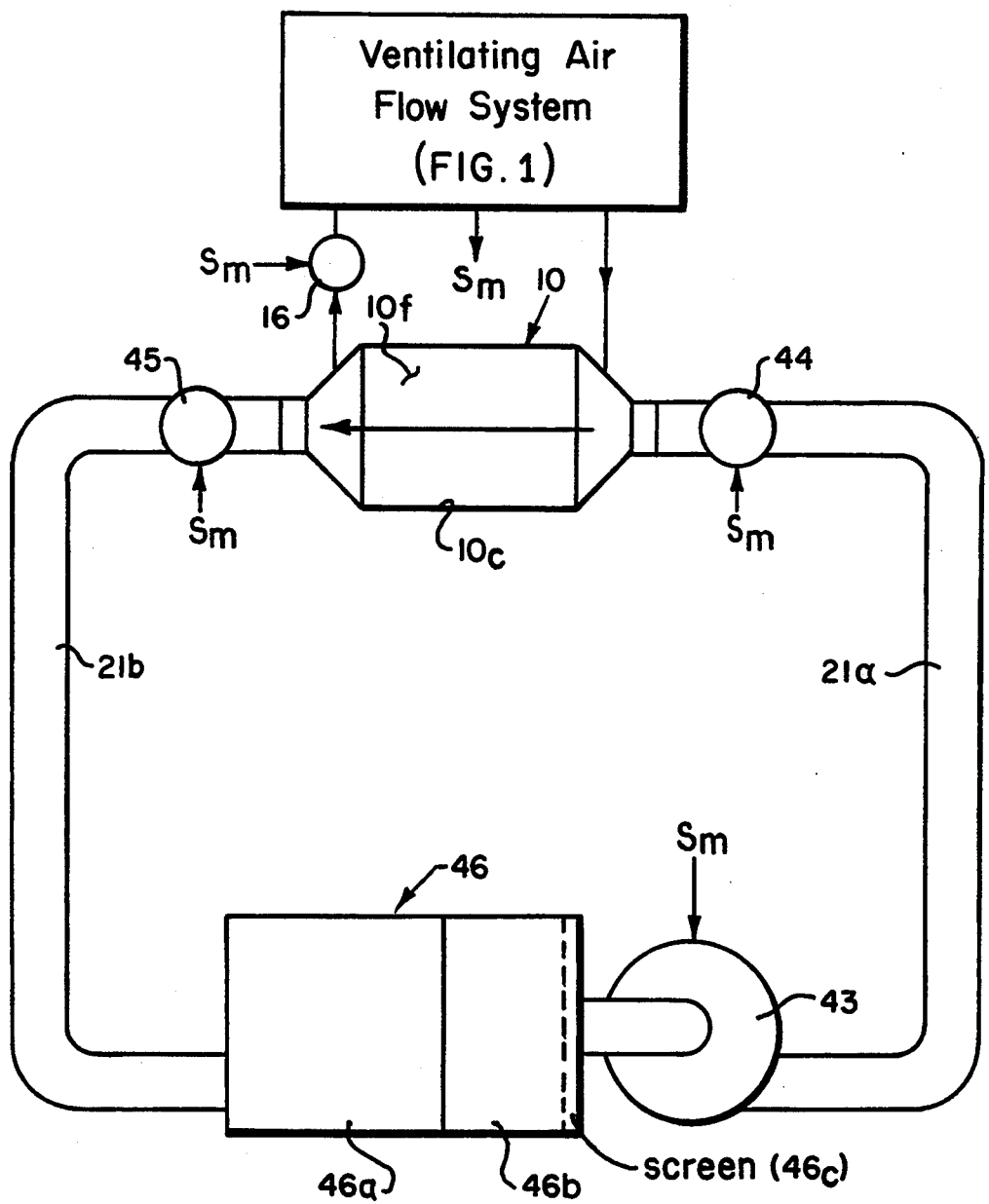
FIG. 3 illustrates major elements of a sweeping air flow and waste removal system shown in FIG. 1.

High velocity air is produced when a fan, shown as a centrifugal air fan 43 in FIG. 3 of the waste removal system 20, is turned on by detection of a step increase in moisture in the ventilating air. A sudden increase in moisture may be readily detected from a ratio of the wet and dry temperature difference $t_w$, $t_d$, of the outlet minipsychrometer 14 to the inlet minipsychrometer 13. When a threshold value of increase in that ratio is detected, a moisture signal $S_m$ is transmitted to the waste removal system 20 to turn on the fan 43. The high velocity air produced by that fan sweeps out liquid and solid animal waste from the calorimeter 10.

As noted with reference to FIG. 1, there are two principal air flow systems associated with the enclosure 10. One system provides ventilating air for the enclosed animal and operates continuously; the other circuit operates on demand and provides a high velocity air flow for waste removal and storage. The latter is activated by the pulse signal $S_m$ from the computer 15 which detects any increase in moisture in the ventilating air at the outlet due to elimination of liquid waste by the animal.

The high velocity air system will now be described in detail with reference to FIG. 3. It comprises: an inlet air valve 44; the enclosure 10E & 10F; an outlet air valve 45; a waste collector 46 comprising a helical urine collection component 46a, an adjacent feces collection component 46b, and a screen 46c. The motor-driven centrifugal air fan 43 referred to above provides the waste removal air flow.

A number of different valve designs and types can be used in the inlet air valve 44 and outlet air valve 45. Some valves could be spring-loaded to open in response to the force of high velocity air from the fan 43, but preferably they are opened by solenoids in response to the pulse signal $S_m$, and returned to the closed condition by a spring when the pulse signal $S_m$ is no longer present. The duration of this pulse signal may be empirically predetermined to complete the task of sweeping the waste material out for either urine or feces, or both.

Figure 4:
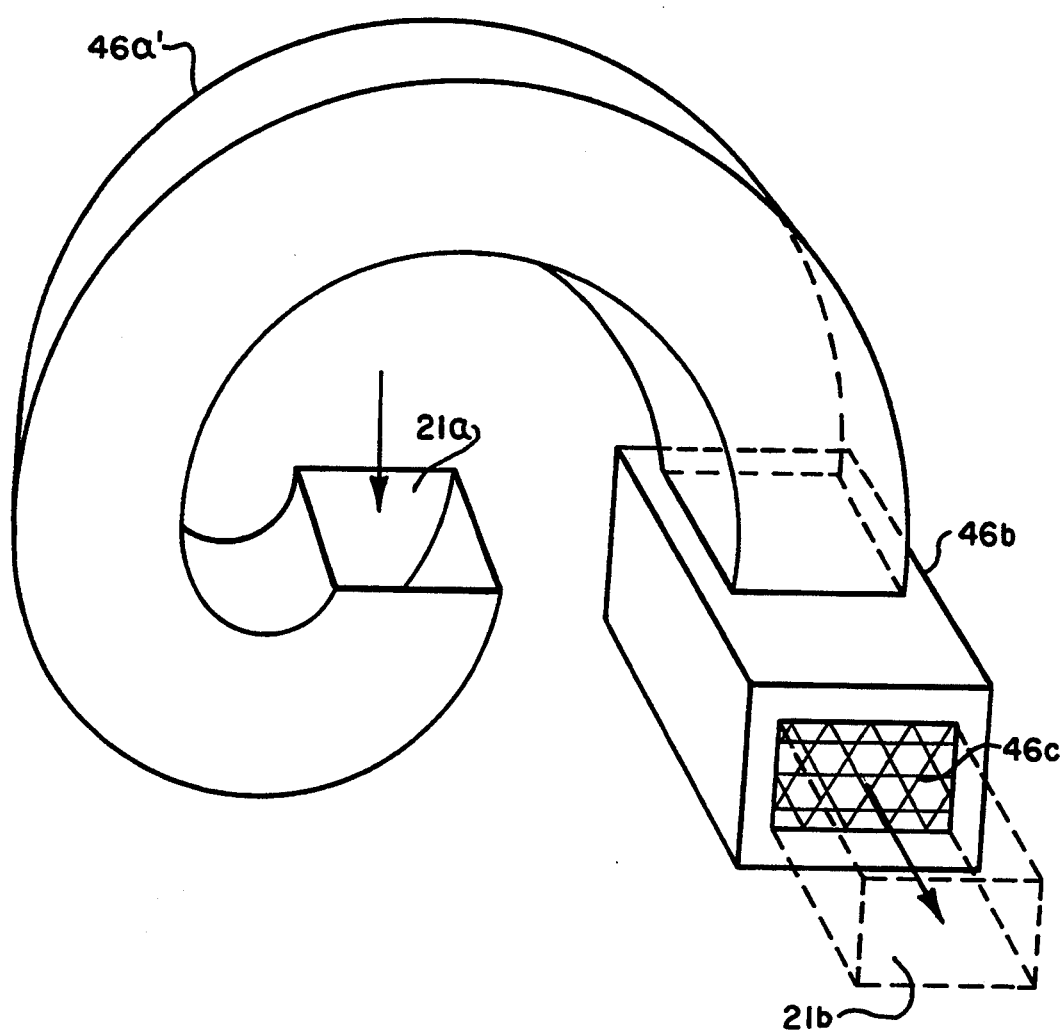
FIG. 4 is an isometric view of a helical air flow channel for centrifugal removal of liquid droplets from sweeping air.

Air flows from the outlet air valve 45 into the urine collection component 46a comprising a helical flow tube 46a' as shown in FIG. 4. There the air containing urine and feces is forced to flow in a helical path so that liquid droplets will be caused to impinge the inside of the outer wall of the tube 46a' by centrifugal force. Absorption material located on that inside surface of the outer wall collects and stores the urine. The feces continues to tumble along in the tube 46a', finally leaving the helical urine collection tube 46a' and entering the feces collecting component 46b, where the screen 46c allows the rotating sweeping air to exit that component, leaving the feces behind.

The motor-driven centrifugal air fan 43 draws the air out of the waste collector 46, pumps the air free of urine and feces through the open inlet valve 44, the enclosure 10e & 10f and then back through the outlet valve 45. An isolation solenoid valve 16 is closed by the pulse signal $S_m$ when the centrifugal air fan 43 is turned on and the solenoid valves 44 and 45 are opened in order to prevent air flow from the waste removal system from flowing through the cabin from which ventilating air is drawn by the air pump 17. At the same time, the pulse signal $S_m$ may be used to turn the ventilating air pump 17 off while the centrifugal air fan 43 is turned on.

At the exit of the centrifugal flow channel 46A is a waste container 46b. Feces swept out of the enclosure will continue to flow through the channel over very flexible leaf springs projecting from the inner wall of the helical channel and bent in the direction of air flow to prevent any motion of feces in the opposite direction between intervals of intermittent flow of high-velocity air. Solid waste matter is separated from the sweeping air by a screen 46c in the container.

The centrifugal flow channel may include odor absorbing material, such as activated carbon, preferably on the inboard surface of the centrifuge flow channel that are not impinged by droplets under centrifugal force. The outboard surface that is so impinged is coated with only material for efficient absorption of liquid waste.

Some of the main features of this waste disposal system design are as follows:

1. The centrifugal flow path has a high enough velocity so that liquid waste is centrifuged to the absorbing material lining the inside surface of the outer wall of the helical urine centrifugal collection component 46a. The drag on the solid waste is strong enough to carry the solid waste into the storage container 46b.
2. The liquid waste absorption material lining has good moisture absorbing properties so that the liquid waste can diffuse within the lining of all walls of the collection component 46a and thus be absorbed throughout the total volume of the lining to accommodate the expected animal liquid waste output during a space mission.
3. The solid waste container 46b is large enough to accommodate the total expected output during a space mission. The screen 46c prevents solid waste material from entering the air fan 43.
4. Odor absorbing material within the centrifuge is so dispensed that it can absorb odors issuing from the moisture absorbing material and the sweeping air stream.
5. Flexible spring-like flow leaves may be placed in the air channel to the waste collector 46 so that backflow of any solid waste left in the air channel during no-flow, zero-gravity conditions is prevented.
6. The surfaces of the animal enclosure 10e, 10f the ventilating air channels, and possibly other components in the system where wetting may be detrimental are coated with hydrophobic material to prevent wetting by any liquid.

There are many materials that are hydrophobic in character in that liquids do not excessively wet them. At the same time, there are, of course, many degrees of wetting and they depend not only upon the liquid surface energies but also those of the solids upon which the liquids are placed. For example, a droplet of mercury deposited on a glass plate exhibits no wetting. If, on the other hand, the droplet of mercury is deposited on a silver or copper surface, wetting occurs. The present invention involves using solid materials that are not significantly wet by urine or any drinking water the animals take but fail to swallow, such that the water becomes a waste liquid that floats in the zero-gravity environment until it comes in contact with a surface. The purpose of the hydrophobic coating on surfaces is to prevent liquid waste from wetting the surface with which it comes in contact, so that sweeping air may carry all liquid into the waste collector 46 where it is captured and stored. Some of the hydrophobic materials are silica, ($SiO_2$), tetrafluoroethylene fluorocarbon polymers (TFE) and fluorinated ethylene-propylene (FET) resins, purified talc (a natural hydrous magnesium silicate), fluoroaliphatic resin, etc.

If a surface is composed of very small, closely spaced, spherical particles, most liquids generally have difficulty in wetting their irregular surfaces. This is because it is too difficult for the liquid to flow into the very small spaces or fissures separating the particles due to the surface tension of most liquids. The result is that the liquids are deployed like a blanket above these very small spaces. Consequently, in order to achieve the greatest degree of hydrophobicity, one should select a material that does not tend to be wet significantly by liquid waste and then deploy that material on a surface to be protected in the form of microspheres (a powder) to generate a network of very small spaces, i.e., narrow surface air passages.

A practical technique for the attachment of the hydrophobic powder to system surfaces in order to create surfaces that will prevent wetting is a problem that has been solved as part of this invention. A series of materials that have low wetting characteristics were identified, and the materials were procured in the form of tiny spheres whose diameters were in the 0.005 to 0.020 micron range. Then methods of attaching such microspheres to surfaces were developed. The method for such an attachment is as follows:
1. A solvent material that partially dissolves the skin of a surface to be treated is applied to such a surface. An alternate procedure is to coat the surface with an adhesive.
2. The powder of a hydrophobic material is added to the treated surface, such as by releasing an aerosol of the material, leaving a coating of microspheres, the unexposed part of which adhere to the soft substrate or the adhesive.

The whole process must be performed in such a way that the hydrophobic spheres are not covered significantly by the dissolved substrate or the adhesive, nor must the air spaces between the microspheres be significantly filled with the dissolved substrate or adhesive. In other words, if too much of the solvent or adhesive material is applied, the hydrophobic material will not form a blanket with fine air passages between the spheres on the surface. When that occurs, the hydrophobic feature is significantly degraded, making it necessary to repeat the treatment.

Tests were conducted on each of several hydrophobic surfaces that were developed to determine the best candidate for the present application. Various size droplets of both actual and simulated urine were deposited on the surface to be tested and the air flows required to completely remove them were recorded. Durability tests were also performed to determine which surfaces could withstand an expected amount of wear without losing their hydrophobic qualities.

The result of the tests led to the discovery of the combination of materials that repel urine and cannot be wet by it. One combination of materials was one part acetone to two parts fumed silica (0.007 micron diameter) mixed thoroughly to form a paste. It was then applied to thin polycarbonate sheeting used as a substrate; the paste was gently rubbed into the surface by hand until all of the acetone evaporated. Another combination of materials again consisted of the paste described above, but it was applied to epoxy type coatings or paints covering calorimeter sensor plates and cage surfaces. Whenever the acetone softened the surfaces of such coatings or paints and the application procedure described above was used, the final hydrophobic surface treatment was successful.

The purpose of the shroud 52 (FIG. 5B) will now be described with reference to FIGS. 5a and 5b. There is a problem that exists with direct (gradient layer) biocalorimeters. Consider an insulated and water cooled gradient layer calorimeter. Further consider no metabolic heat source within the calorimeter enclosure but ventilating air flowing into it. As changes occur in air temperature within the room and the ventilating air is drawn into the calorimeter enclosure from the room, there will always be a nonzero calorimeter output signal.

When an animal or human is put into the calorimeter enclosure and such fluctuating room air temperatures are operative, it is difficult to determine whether calorimeter output signal changes relate to metabolic terms or fluctuating inlet room air temperatures. Although this problem is not a major one, it does limit the degree of accuracy that one can achieve with such a system. In order to obviate this problem, the air temperature in the room in which the calorimeter is housed is normally air conditioned or so controlled that air temperature changes do not occur, thus yielding no fluctuating calorimeter output signals.

Many environments in which biocalorimeters of this type are used cannot be accurately controlled as ideally desired, such as in a spacecraft cabin. Therefore, the following solution to the problem has been conceived. Specifically, the water cooling system and insulation around a gradient layer calorimeter are completely removed so the animal or human enclosure (typically an aluminum envelope), which contains an inner heat flux sensor envelope, is completely bare and exposed to environmental air temperature.

Now consider the same example discussed above, namely, allow environmental air to be drawn into the calorimeter flux sensor envelope with no metabolic heat source in the calorimeter envelope. If the environmental air temperature were to change in some arbitrary variable way, it would also change within the calorimeter by the same amount as the surrounding air drawn into the calorimeter envelope and hence, no significant temperature difference would exist across the composite aluminum enclosure and inner flux sensor envelope. Hence, the calorimeter output signal would show a zero output, or one very close to zero, in contrast to a significant millivolt signal in the case of an insulated and water-cooled calorimeter.

This simple but very important principle has been demonstrated when environmental air temperature changes 10° F. over a 7-10 hour period, yet millivolt output signal changes were only 1% of the magnitude of the metabolic output signals that occurred when typical laboratory animals were in the calorimeter. Shrouding the calorimeter system diagrammatically illustrated in FIG. 1 will make it possible to more accurately measure heat releases from laboratory animals and humans in environments whose air temperature cannot be regulated for a variety of reasons, as will now be described with reference to FIGS. 5a and 5b.

FIG. 5a shows the simplest geometrical deployment of a biocalorimeter envelope. In this arrangement, the biocalorimeter is located in a space where the air temperature, $t_a$, which surrounds the calorimeter is varying in some arbitrary fashion with time. There are no strong radiation sources (such as heaters) or radiation sinks (such as cold windows) in the space (cabin of a spacecraft, for example).

FIG. 5b illustrates an alternative geometrical deployment of a calorimeter 49 envelope relating to the situation when there are strong varying radiation sources or radiation sinks present in the space. For such circumstances, a biocalorimeter may comprise a standard aluminum enclosure 50 with an inner flux sensor envelope 51 and a thin outer shell 52 placed as a shroud around the animal enclosure to shield the surface of the enclosure 50 from the radiant heat sources and sinks. For this arrangement, the ventilating air is drawn into the flux sensor envelope 51 through the air space between the radiation shield 52 and the outer surface of the aluminum enclosure 50. Again, the major principle of nulling out the convective heating or cooling of the ventilating air as it passes through the calorimeter system prevails, with the added advantage of shielding the biocalorimeter from radiant heat sources and sink.

Two new applications for this shrouding technique for biocalorimeters are particularly noteworthy. One is a small whole body calorimeter in medical offices where room temperatures are not very accurately controlled, but where it is desirable to obtain information on patients in a relatively short period of time and by means of less complicated and expensive systems than some of the current insulated and water-cooled whole body calorimeters. A second application relates to space biocalorimeters. In the event that the temperature of the environmental air in a space vehicle orbiting the earth varies as the earth passes between the vehicle and the sun, a shrouded calorimeter system solves the problem of obtaining the accurate measurements that would otherwise be difficult to obtain by even the more complex insulated and water-cooled system.

Although particular embodiments of the invention have been described and illustrated herein, it is recognized that modifications and variations may readily occur to those skilled in the art. Consequently, it is intended that the claims be interpreted to cover such modifications and equivalents.

We claim:

1. A biocalorimeter and waste management system for making metabolic heat release measurements of small animals in zero-gravity space of a spacecraft having air for maintaining the life and comfort of said animals, comprising an enclosure for said animals undergoing metabolic heat release measurements, said enclosure having an inlet and an outlet through which air can circulate, thermopiles attached to a wall of said enclosure for producing a signal representing a temperature difference across said wall from the inside to the outside of said enclosure as a measure of heat released by said animals, a shroud around said enclosure and thermopiles for shielding said enclosure and thermopiles from radiant heat sources and heat sinks outside of said enclosure, means for circulating ventilating air from said zero-gravity space through said inlet and outlet of said enclosure, a first psychrometer at said inlet for producing a signal representing a difference between wet- and dry-bulb temperature measurements of said circulating ventilating air into said enclosure through said inlet, a second psychrometer at said outlet for producing a signal representing a difference between wet- and dry-bulb temperature measurements of said circulating ventilating air out of said enclosure through said inlet, means responsive to said signals produced by said first and second psychrometers for removing animal waste from said enclosure comprising , a separate recirculation channel for high velocity air through said enclosure, means for producing said high velocity air through said separate recirculation channel in response to a step increase in moisture detected by comparison of said signal produced by said second psychrometer with said signal produced by said first psychrometer, and for producing a signal representing air flow rate of such high velocity air produced, and means for separating and capturing liquid and solid animal waste from said high velocity air, and means for calculating metabolic heat release from said small animals out of said enclosure in response to said signals produced by said first and second psychrometers, said air flow rate signal, and said temperature difference signal from said thermopile representing heat flowing through said wall of said enclosure to the exterior of said enclosure.

2. A system as described in claim 1 wherein said high velocity air means comprises an air blower driven by a motor activated by means for generating a moisture sensed signal in response to a sudden difference between said signals produced by said first and second psychrometers.

3. A system as defined in claim 2 wherein said high velocity air means comprises a channel for redirecting high velocity air through at least 180°, absorbing material in said channel in order to cause droplets of liquid animal waste entrained in said high velocity air to be separated from said high velocity air by a centrifugal force in order to be absorbed by said material.

4. A system as defined in claim 3 wherein said high velocity air means further includes a container for capturing solid waste material carried by said high velocity air out of said channel, said container having a screened opening for passage of said high velocity air out for recirculation through said separate recirculation channel.

5. A system as defined in claim 4 wherein said enclosure is provided with a pyramidal shape for said inlet and outlet of ventilating air, said inlet and outlet being disposed directly opposite each other on said enclosure, and valve means at said inlet and at said outlet for closing off said ventilating air into and out of said enclosure in response to said motor being activated to produce high velocity air while coupling said enclosure into said separate recirculation channel for high velocity air to sweep through said enclosure.

6. A biocalorimeter for metabolic heat release measurements of a body comprising an enclosure for said body, said enclosure being formed of metal which serves as a heat sink, a heat flux sensor envelope supporting thermopile means within said enclosure in a path through which heat release flows to said heat sink for heat release flow measurement, a ventilating air inlet means at one end of said enclosure for allowing flow of ambient air from outside of said enclosure, a ventilating air outlet at an end of said enclosure opposite said one end, and a shroud surrounding said body enclosure, said shroud being open to said ambient air proximate said ventilating air outlet at said end of said enclosure opposite said one end, and closed around said body enclosure at said one end to restrict ventilating air into said enclosure at said one end to ventilating air passing through said open end of said shroud and over said enclosure to said one end of said enclosure, whereby direct metabolic heat measurements of a body in said enclosure may be made by said thermopile means without imposing stabilizing control of said ambient air temperature.

7. A biocalorimeter as defined in claim 6 including means for measuring dry- and wet-bulb temperature of ventilating air passing through said inlet means, and means for measuring dry- and wet-bulb temperature of ventilating air passing through said outlet, thereby making it possible to account for the sensible and latent heat additions to said ventilating air by said body.

* * * * *